United States Patent [19]

Cook

[11] Patent Number: 5,004,476
[45] Date of Patent: Apr. 2, 1991

[54] POROUS COATED TOTAL HIP REPLACEMENT SYSTEM

[75] Inventor: Stephen D. Cook, New Orleans, La.

[73] Assignee: Tulane University, New Orleans, La.

[21] Appl. No.: 445,920

[22] Filed: Oct. 31, 1989

[51] Int. Cl.⁵ .............................................. A61F 2/36
[52] U.S. Cl. ..................................................... 623/23
[58] Field of Search ...................... 623/16, 18, 19, 20, 623/22, 23

[56] References Cited

U.S. PATENT DOCUMENTS

| | | |
|---|---|---|
| 3,521,302 | 7/1970 | Muller . |
| 3,584,318 | 8/1971 | Scales . |
| 3,605,123 | 9/1971 | Hahn . |
| 3,840,904 | 10/1974 | Tronzo .................................. 623/23 |
| 3,855,638 | 12/1974 | Pilliar . |
| 3,906,550 | 9/1975 | Rostoker et al. . |
| 3,986,212 | 10/1976 | Sauer . |
| 4,164,794 | 8/1979 | Spector et al. . |
| 4,172,296 | 10/1979 | D'Errico . |
| 4,179,485 | 12/1979 | Tritten . |
| 4,206,516 | 6/1980 | Pilliar . |
| 4,281,420 | 8/1981 | Raab . |
| 4,336,618 | 6/1982 | Raab . |
| 4,351,069 | 9/1982 | Ballintyn et al. . |
| 4,355,428 | 10/1982 | Deloison et al. . |
| 4,365,358 | 12/1982 | Judet ..................................... 623/22 |
| 4,365,359 | 12/1982 | Raab . |
| 4,406,023 | 9/1983 | Harris ..................................... 623/23 |
| 4,514,865 | 5/1985 | Harris . |
| 4,528,980 | 7/1985 | Kenna . |
| 4,536,894 | 8/1985 | Galante et al. . |
| 4,542,539 | 9/1985 | Rowe, Jr., et al. . |
| 4,589,883 | 5/1986 | Kenna ..................................... 623/22 |
| 4,612,160 | 9/1986 | Donlevy et al. . |
| 4,619,658 | 10/1986 | Pappas et al. . |
| 4,636,214 | 1/1987 | Homsy . |
| 4,644,942 | 2/1987 | Sump ..................................... 623/16 |
| 4,666,450 | 5/1987 | Kenna ..................................... 623/22 |

OTHER PUBLICATIONS

An article entitled "Interface Mechanics and Bone Growth into Porous Co-Cr-Mo Alloy Implants", by Cook et al.; Clinical Orthopedics, Mar. 1985; vol. 813, pp. B-1 to B-10.
"The Total System", Brochure published by Zimmer, pp. 1-23.

*Primary Examiner*—David J. Isabella
*Attorney, Agent, or Firm*—Nixon & Vanderhye

[57] ABSTRACT

Hip joint prosthesis for replacing diseased or defective joints including a femoral stem, vacuum cast of cobalt-chromium-molybdenum and hot isostatically pressed (HIP'd) both before and after porous coating to provide an additional 50% greater strength in high cycle fatigue loading than all comparable porous coated devices of prior art, with optimal porous coating parameters scientifically and clinically determined for 75% greater fixation than all comparable devices of prior art, anatomically shaped and easily constructed in right and left configurations and a range of sizes, a femoral head which attaches to the stem intraoperatively, and an acetabular component consisting of a polymer bearing-type insert mechanically fixed inside a metal shell, the bearing surface articulating with the femoral head.

25 Claims, 2 Drawing Sheets

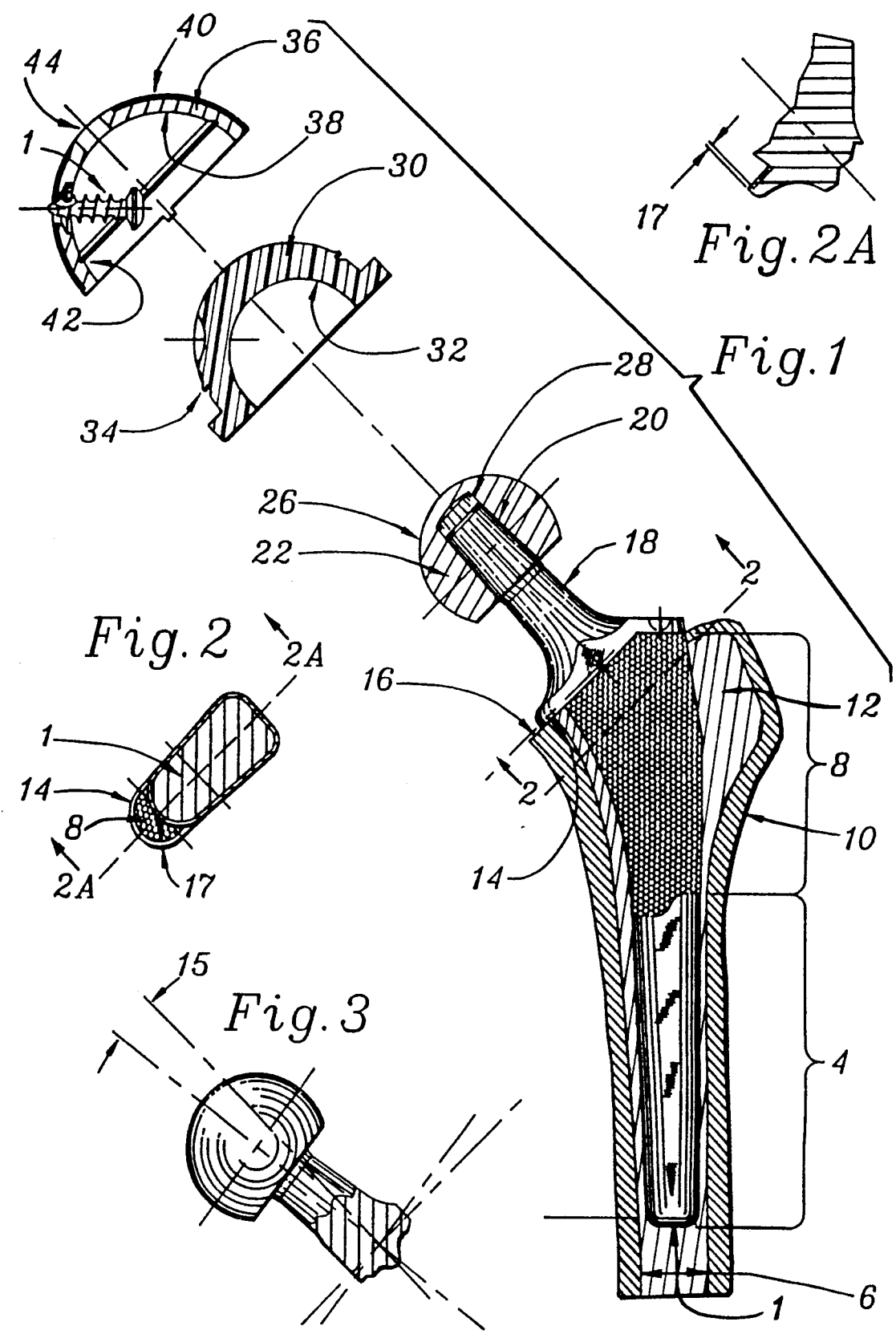

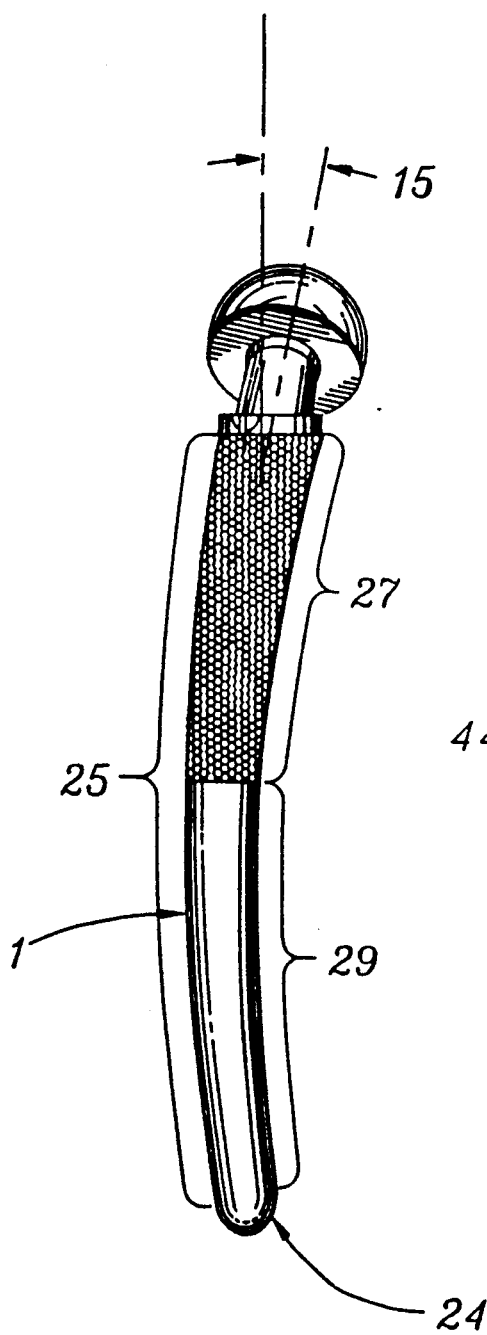
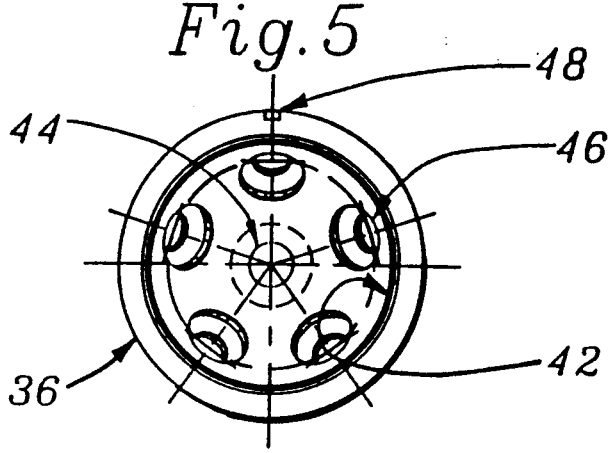
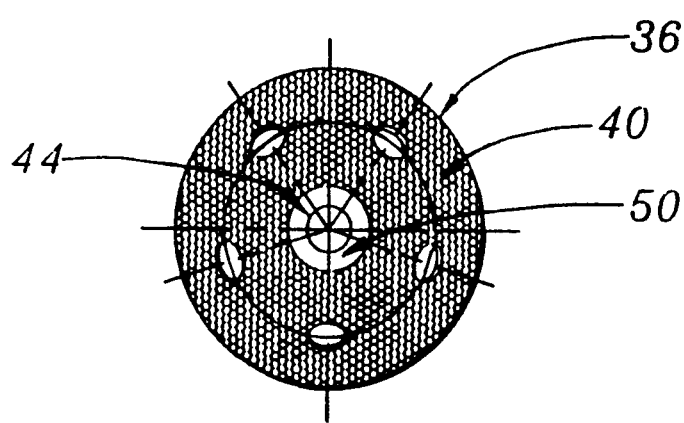
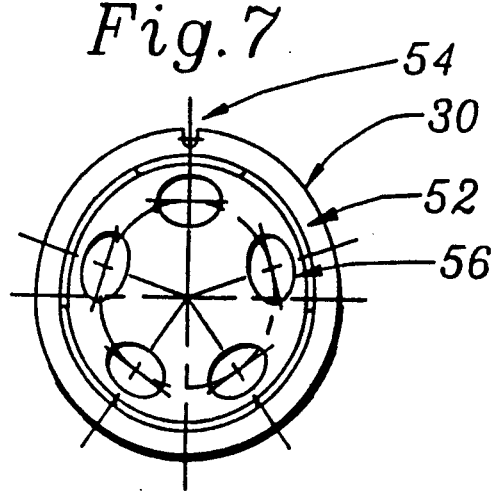

POROUS COATED TOTAL HIP REPLACEMENT SYSTEM

This is a continuation of U.S. application Ser. No. 07/145,278, filed Jan. 19, 1988, now abandoned.

This invention relates to prosthetic devices and, more particularly, to a hip joint metal/polymer semi-constrained prosthesis to replace a diseased or otherwise defective hip joint of a patient, and is intended for reconstruction of painful and/or severely disabled hip joints. The hip joint is made of compatible, well tolerated biomaterials.

BACKGROUND OF THE INVENTION

Prosthetic hip joint devices, such as the P.C.A. hip system distributed by Howmedica, Inc. and the APR Universal System distributed by Intermedics Orthopaedics, are known and in wide use in current medical practice.

The insertion and attachment of prosthetic devices may be either cemented, using bone cement, or through ingrowth of surrounding bone into the prosthesis/bone interface. More recently, the use of uncemented joint replacements has been favored as surgeons wish to avoid the use of bone cement and its attendant difficulties and potential complications. In order to achieve appropriate bone ingrowth, porous coatings are used on various portions of the prosthetic device. Porous metal coatings for surgical prosthetic devices are described in U.S. Pat. No. 3,855,638 to Pillar. The porous coated structure encourages bone ingrowth and enhances cement fixation; however, fixation is preferably achieved biologically with bone ingrowth.

A porous coating in itself will not ensure that the surgeon's goal, i.e., long-term fixation, is realized in order to avoid early failure and subsequent revision. Existing porous-coated systems do not properly address this problem because: (1) prior total hip systems are not stabilized initially because of problems such as micro movement, subsidence and torsional loosening and, (2) imprecise coating of the prosthesis can cause a phenomena known as "stress shielding" and loosening which, when they occur, can lead to catastrophic failure in a relatively short time after implantation.

Also, prior femoral stem implants limit the area of porous coating to the calcar region; the implant is usually set in soft cancellous bone. With many prior femoral stem implants, clinicians have reported a significant incidence of subsidence or sinking of the prosthesis stem portion into the femur. Any subsidence is usually viewed as a failure, since it can cause severe patient pain and result in loosening and eventual replacement or the prosthesis. In many cases fibrous tissue attachment, not true bone ingrowth, results and thus may contribute to implant loosening and failure.

The total hip system of the present invention provides a combination of the correct prosthetic design to stabilize the hip immediately upon implantation and specific placement of the porous coating, both carefully selected to overcome the risk of loosening and stress shielding.

The total hip system described herein includes three essential components. They are (1) a femoral stem, anatomically shaped and easily constructed in right and left configurations and a range of sizes, (2) a femoral head which attaches to the stem intraoperatively, and (3) an acetabular component consisting of a polymer bearing-type insert mechanically fixed inside a metal shell, the bearing surface articulating with the femoral head.

An object of the present invention is to provide a porous coated total hip replacement system having initial stability so that bone in-growth can occur and a porous metal coating in predetermined regions with an appropriate structure that encourages bone ingrowth and/or enhances cement fixation to the required location. An anatomically designed femoral stem with a collar which is coated on the underside for added cortical fixation, physiological stress transfer and prevention of subsidence and a cooperating acetabular component to provide the optimum success rate for implanted devices are combined with a porous ingrowth area strategically located in the proximal femoral region to result in not only ingrowth of the soft cancellous bone, but also adequate ingrowth of hard, true cortical bone tissue. The acetabular component is provided with both a porous coating and also means for mechanical attachment and fixation to the pelvis via screws or other fastening devices.

A porous metal coating is located in the upper proximal half of the femoral stem and is selected to be applied at a suitable thickness of an optimal pore size and with the appropriate porosity to ensure compatibility with and ingrowth by the surrounding bone tissue. The femoral stem component of the total hip replacement system is designed to anatomically fill the femoral canal, is provided in both left and right hand configurations, and causes minimal bone stock removal. The anatomically designed femoral stem with collar serves to resist torsional loosening by means of its curvature and rectangular/triangular anterior/posterior cross section to stress the calcar physiologically, provide a calcar cortical in-growth interface and to reduce subsidence of the stem into the bone which, together with the placement of the porous coating extending into the femoral cortical or hard bone, serves to further prevent subsidence of the stem. These multiple features are important and must be used in combination in order to achieve best results, for a collarless anatomical stem even when provided with the porous coating can contribute to torsional loosening if it has a rounded cross-section and if the porous coating is limited to the soft cancellous bone. Thus, the stem component of the porous coated total hip replacement of the present invention provides a curvature with rectangular/triangular anterior/posterior cross-section and a porous coating that extends into the proximal cortical area of the femur and thereby effectively resists torsional loosening.

The design of the femoral stem in accordance with the invention is also selected to minimize or avoid subsidence or sinking of the implant into the femur while maintaining fixation strength that can only be achieved with an implant that is fixed both to the cancellous and the cortical bone and in combination with a medial collar reinforced for initial stability of the implant with porous coating on the underside to provide added cortical ingrowth, physiological stress transfer and to further prevent subsidence. Fixation to the cortical bone is a particular advantage since it serves to transfer stress from the prosthesis to the adjacent cortical bone as well as to adjacent cancellous bone. Absence of successful stress transfer, for instance fixation only to the cancellous area, will invite difficulties such as stress shielding, subsequent loosening and subsidence. Although adapted to be used either with or without bone cement, the porous coated total hip replacement system of the present invention may be successfully used as an uncemented joint replacement and a stable bone/prosthesis interface results.

The total hip replacement system as described herein is intended for reconstruction of painful and/or severely disabled hip joints resulting from osteoarthritis, rheumatoid arthritis, traumatic arthritis, avascular necrosis and other conditions, or as a replacement for previously failed prostheses. The device according to this invention employs an anatomically shaped stem whose curvature closely follows the proximal portion of the femur thus minimizing bone removal while providing for uniform stress transfer. The undercoated collar enhances stability of proximal fixation, physiological stress transfer proximally and provides security against subsidence. Pore size, thickness and placement of the porous coating provide optimum long term fixation and stress distribution while providing a stable interface for bone ingrowth.

The total hip replacement system has unique advantages which, in the hands of the orthopaedic surgeon, restores the patient to naturally functioning, pain-free mobility. The unique features of the system are the initial stability of the implant which allows in-growth to occur, the specific porous coated parameters of pore size, pore volume and the specific placement of the porous coating interface on the femoral stem, the femoral stem collar and acetabular cup to facilitate long term stability and vacuum casting of the femoral component to provide added strength in high cycle fatigue loading.

BRIEF DESCRIPTION OF THE DRAWINGS

The invention will be further illustrated with reference to the attached drawings in which:

FIG. 1 is an exploded posterior view of the right femur porous coated total hip replacement system of the present invention the promixal portion of the right femur shown in cross section;

FIG. 2 is a cross sectional view of the femoral stem along line 2—2 of FIG. 1 showing the calcar collar;

FIG. 2A is an enlarged detailed view of the lip that surrounds the underside of the collar to protect the porous coating thereon;

FIG. 3 is an enlarged view of a neck angle in accordance with the invention;

FIG. 4 is a lateral view of the stem of FIG. 1 rotated 90° showing the shaping of the curve to anatomically fill the canal of the right femur;

FIG. 5 is an inside plan view of the metal acetabular cup backing of the system;

FIG. 6 is a top plan view of the metal acetabular cup backing of FIG. 5 showing porous coated area and FIG. 7 is a top plan outside view of the smooth plastic acetabular cup insert.

DETAILED DESCRIPTION OF THE DRAWINGS

As shown in the exploded view in FIG. 1, the porous coated total hip replacement includes a femoral stem 1 that is inserted into and later becomes fixed to the proximal portion of the patient's femur (as shown in cross section). During insertion, the proximal portion of the femur is prepared by removal of extraneous tissue and bone (not shown) and the entire stem is inserted into the femoral canal 6. The shank portion 4 is smooth cobalt chrome molybdenum alloy, while the proximal portion 8 of the stem is covered with sintered beads of cobalt chrome molybdenum alloy as described in more detail below. Stem 1 is received in the femur with the porous coated portion in contact with the cortical areas in the calcar and proximal femur 10 as well as the soft cancellous bone 12. Stem 1 includes a calcar collar 14 that is porous coated on the underside with a surrounding lip to contain and protect the porous coating from fatigue fracture and extends inward of the stem and contacts and rests on the adjacent calcar area 16 of the bone. Projecting from stem 1 is a neck 18 provided with a tapered end 20 known as a Morse taper. The previously referenced porous coating provides a surface of interconnected three dimensional pores with which bone or bone cement can achieve a secure, stable mechanical interlock. The stem 1 is coated only on the proximal portion 8 with a medial collar 14 porous coated on the underside for additional fixation stability to provide long-term proximal physiological stress transfer and to prevent subsidence. Should removal ever become necessary, this is facilitated through free access to the lateral, anterior, and posterior aspects of the implanted portions of the stem 1, since the collar 14 does not extend to these areas. The most proximal portion of the neck is ground to a small angle taper to interlock with the appropriate femoral head 22 which may be determined intraoperatively.

A cooperating femoral head 22 having a smooth spherical ground and polished outer surface 26 fits over the tapered portion 20 of the stem with a cooperating and mating opening 28. The two surfaces "weld" together when installed. It will be appreciated that the length of neck 18 may be varied and will range from 25 mm to 43 mm or so measured from the base of collar 14 to the center line of the femoral head 22, thus providing variable distances between the end of the femur and the outermost portion of the smooth spherical surface 26 of head 22.

In FIG. 2, porous coating 8 covers the underside of collar 14 and the proximal circumference of stem 1. Lip 17 surrounds the underside of collar 14 and protects porous coating 8 on underside of collar from fatigue fracture.

In FIG. 2A, lip 17, 1 mm in width is shown in cross section.

FIG. 3 is an enlarged detailed view of the 8° neck angle 15, as it extends medially from the base of the collar 14, which angle reflects the centerline CL direction of the confluence of the posterior 25 and proximal 27 and distal 29 anterior surfaces of the stem body, which arcs which form the anatomical curve as depicted in FIG. 4.

The completed acetabular cup assembly is attached to the patient's pelvis and receives the head of the smooth, circular femoral head attached to the stem neck 18. The acetabular metal component 36 receives a smooth, inert, wear-resistant plastic acetabular cup insert 30 having an inside surface 32 corresponding to the outer smooth surface 26 of head 22. Preferably the insert is made of ultra high molecular weight polyethylene. Cup insert 30 receives head 22 and allows free rotation with minimal friction inside the acetabular cup assembly. The insert 30 is approximately hemispherical in shape, with external snap ring 34 is mechanically fixed inside the metal acetabular cup 36 and allows the femoral head 22 to articulate freely in ball-in-socket fashion.

The acetabular metal component 36, nearly hemispherical in shape, is in turn, secured to the patient's pelvis by either bone cement, press fit, mechanical fastening devices such as a self-tapping surgical screw 19 or the like. The metal cup backing 36 has an inside surface 38 that is relatively smooth and an outside porous coated surface 40 that is almost entirely covered with sintered beads of cobalt chrome. The actetabular metal cup backing 36 has an internal snap ring groove 42 to cooperate and secure the external snap ring groove 34 of insert 30. A centrally located sighting hole 44 is provided in the acetabular cup for proper placement and to assure uniform intimacy with adjacent bone. Porous surface 40 serves to attach the metal cup backing 36 to the patient's pelvis by ingrowth or cement and is shown in more detail in FIG. 6.

FIG. 4 is a view of stem 1 rotated 90° showing the anatomical curve of the stem designed to fill the femoral canal and also showing a relieved distal tip 24 of stem, also referred to as a "flattened anterior tip", to prevent impingement upon cortices and consequent mid-thigh pain. The design of the curve is specific to either a right or left configuration and is chosen to require only minimal bone stock removal for successful implantation. A right stem is shown in this figure.

FIG. 5 is an inside view of the acetabular metal cup backing 36 showing one central sighting hole 44 and five counter-sunk, radially positioned openings 46 to secure the metal cup to the acetabulum with suitable fastening means, for instance, surgical screws. The outside rim of metal cup 36 has a key 48 (projecting outwardly from the plane of the drawing) which prevents rotation of the plastic insert 30 when inserted and received by the metal cup backing.

FIG. 6 is a top outside view of the metal cup backing 36 showing the porous coating 40 on virtually all of the surface except for a central uncoated zone 50 which is a smooth metal alloy and has no porous coating. This uncoated area is to facilitate removal of the acetabular metal cup backing 36 from the patient should this become necessary. Holes 46 are radially positioned to allow maximum flexibility for the surgeon, to assure uniform intimate attachment to the adjacent bone material and to allow for symmetrical fixation of the metal acetabular component.

FIG. 7 is a top view of acetabular cup insert component 30 showing an outer rim 52 and a keyway 54 for receiving key 48 projecting from the metal acetabular cup backing 36 in order to properly position the plastic insert. Key 48 and keyway 54 prevent the acetabular cup insert component 30 from rotating in the metal acetabular cup backing 36. The outer surface of the plastic cup insert is provided with spherical relief recesses 56 which together with counter-sunk holes 46 provide clearances for the metal screws or other fastening devices when the metal cup backing and the plastic insert are assembled together. The plastic cup is made of ultra high molecular weight polyethelene, or may be made of other suitable material. The plastic cup insert is provided with an outwardly projecting snap ring fitting 34 to be received in groove 42 sleeve to insert 30 into metal cup 36. Once positioned and snapped into place, it is difficult to remove the plastic cup insert inadvertently. The inside surface 32 of the plastic cup insert 30 in contact with metal head 22 is a smooth spherical surface that allows the smooth, highly polished metal head 22 to rotate freely and smoothly inside this plastic cup.

A left or right femoral stem which is vacuum cast in cobalt chrome alloy, coated circumferentially with sintered beads of cobalt chrome over the proximal half of the stem is illustrated in FIGS. 1 and 4. This coating provides a surface of interconnected three dimensional pores with which either bone growth or bone cement can achieve a secure mechanical interlock. Placement of the porous coating on the stem 1 and under the collar 14 is one of the more significant factors in achieving sound fixation, providing physiological stress transfer and to avoid prosthesis subsidence. The porous coating is judiciously placed on the stem in the cancellous bone area 12 and is extended distally into the proximal cortices 10, as well as under the collar 14 for calcar cortical ingrowth.

The acetabular cup has an outer shell of porous coated metal alloy beads sintered onto the underlying metal alloy and an inside bearing surface of ultra high molecular weight polyethylene. Fixation screws are provided for security and stability during the post-operative pre-ingrowth phase when the cup is used without cement.

As it is an object of this invention to provide a prosthetic device that accomplished fixation by bone ingrowth, the material from which the device is made is inert to the surrounding tissue and has a porous structure with a pore size on the order of 250–300 $\mu$m. The appropriate pore size is determined in accordance with the procedures described by S.D. Cook et al., Intertace Mechanics and Bone Growth into Porous Co-Cr-Mo Alloy Implants *Clinical Orthooaedics*, Vol. 183, pp. 271–280, March 1985.

The total vacuum cast hip replacement system of the present invention employs a metal alloy stem that anatomically fits the femoral canal, is configured in both left and right configurations and is designed so as to require minimal bone stock removal for satisfactory placement and attachment. The stem is provided with a porous coating of sintered beads of a bio-compatible metal alloy, and provides an interconnected 3-dimensional network to allow bone growth or the use of bone cement, depending upon the choice of the surgeon. This coating is provided on the proximal half of the stem and, when inserted into the patient, extends not only into the soft cancellous bone in the calcar, but into the cortices or hard bone and, by design of the undercoated collar, onto the cortical bone of the calcar area. The combination of an anatomical stem and porous coating extending into the cortical area and onto the calcar enables the stem to resist torsional loosening, provides physiological stress transfer, and provides an additional area for cortical ingrowth under the collar. In addition, the collar, in contact with the calcar region of the femur, prevents the implant from sinking into the femur, a term known as "subsidence".

As compared with prior devices, the porous coated total hip replacement system of the present invention achieves a level of fixation strength that is up to 75% greater than comparable implants. This is achieved by fixation both in the cancellous and cortical bone areas and serves to provide physiological stress transfer from the implant directly to cortical bone located in both the calcar and proximal femur. Absent good fixation, stress shielding and subsequent loosening of the implant may occur, which is a particular problem with implants whose porous coating is restricted only to the cancellous bone interface, and without an undercoated collar. In particular, applicants implant is designed for uncemented joint replacement, and as such provides a stable bone/prosthesis interface, the porous coating providing an interconnected three dimensional network that is hospitable to bone ingrowth and the resulting mechanical interlock.

DESCRIPTION OF THE PREFERRED EMBODIMENT

The implant is prepared by vacuum casting and hot isostatic pressing (HIP'ing), a cobalt-chromium-molybdenum alloy (ASTM-F-75) using the lost wax process. First a replica of the desired product is made of wax and this wax pattern is coated with several layers of a ceramic slurry. The layers are built one atop the next until a robust ceramic mold is formed around the wax pattern. The wax pattern is then melted away, leaving a cavity in the ceramic that is an exact replica of the original wax shape. The ceramic is then fixed and a molten alloy is poured into the mold cavity under vacuum conditions. The alloy is allowed to solidify, then cooled, the ceramic removed and the vacuum cast product, either in the form of a stem, acetabular cup or femoral head results, followed by the previously referenced and otherwise conventional hot isostatic pressing (HIP'ing) process, the vacuum casting and HIP'ing combination providing a additional 50% greater strength in high cycle fatigue loading than all comparable porous coated devices of prior art.

A porous coating is then applied by placing two layers of cobalt-chromium-molybdenum alloy (ASTM F-75) particles on the casting in the position desired using an organic binder or glue to temporarily hold the particles in place. The casting with porous coating attached is then heated to a temperature sufficient to create interparticle bonds or welds and particle-to substrate bonds which create a three dimensional porous network on the surface, after which the HIP'ing process is repeated. In the preferred aspect of this invention, the resultant porous coating is at least 1 mm thick and has a pore size of approximately 300 μm and a pore volume of between about 40 and 50%, preferably about 45%. The component then undergoes various machining operations which includes the creation of a taper on the neck of the femoral component which, by way of a very small angle (approximately 6°), allows the creation of a secure fit with the femoral ball portion of the device.

As presently envisioned, the total hip system consists of three basic components: a femoral stem, which is available in right and left configurations and a range of sizes to fit varying patient anatomical requirements, vacuum cast followed by the HIP'ing process, wherein the vacuum casting and HIP'ing process combination provide an additional 50% greater strength in high cycle fatigue loading than all comparable porous coated devices of prior art; a femoral head, available in 32 mm outside diameter and three neck lengths, which attaches to the stem intraoperatively with a Morse taper fit; and an acetabular component consisting of a polymer bearing insert backed by a metal shell which is also available in a range of outside diameters.

A porous coating of cobalt-chromium-molybdenum beads is affixed by a sintering process to all sides of the proximal 45% of the stem and then the HIP'ing process is repeated. This coating provides a surface of interconnected three dimensional pores with which either bone or bone cement can achieve a secure, stable mechanical interlock. The stem is coated only on the proximal portion with a medial collar porous coated on the underside for additional fixation stability, to provide long-term physiological stress transfer proximally and to prevent subsidence.

The femoral head is also investment cast in cobalt-chromium-molybdenum alloy conforming to ASTM F-75. The outer bearing surface is spherically ground and finished to a high polish. The inner surface of the head is ground to a small angle taper to mate with the femoral head.

The outer shell of the acetabular cup is also investment cast in cobalt-chromium-molybdenum alloy conforming to ASTM F-75. It is approximately hemispherical in shape and its outer surface is porous coated by the same process as the femoral stem. An ultra-high molecular weight polyethylene (UHMWPE) bearing surface which articulates with the femoral head is mechanically fixed inside the metal shell to complete the acetabular component.

All three implant components are provided presterilized by exposure to a minimum of 2.5 megarads of gamma radiation.

Other embodiments of the invention will be apparent to one skilled in the art from a consideration of the specification or the practice of the invention disclosed herein. It is intended that the specification and examples be considered as exemplary only, with the true scope and spirit of the invention being indicated by the claims.

What is claimed is:

1. A hip joint prosthesis comprising, in combination:
   an inert metal alloy intramedullary stem having posterior, proximal anterior and distal anterior surfaces defined by respective confluent arcs which enable said stem to anatomically conform to the femoral canal, the stem having a medial collar adjacent an upper end of a proximal portion, the collar extending medially outwardly from the stem for engagement with the calcar region of the femur, said upper end terminating in a tapered shaft adapted to receive a femoral head component, the stem having a smooth distal portion with a lower end flattened to form an anterior stem tip to avoid impingement with the cortices, thereby preventing distal loading and consequent mid-thigh pain; a porous coating of metal beads providing a porous surface of interconnected three dimensional pores over the proximal portion of the stem and an underside of said medial collar, said coating adapted to mechanically interlock the proximal stem area with both soft cancellous and hard cortical bone tissue of the femur;
   an inert metal alloy femoral head having a smooth substantially spherical outer bearing surface and adapted to be attached to the tapered shaft of the stem, intraoperatively;
   an inert metal alloy acetabular cup for attachment to the acetabulum having a substantially hemispherical shape and inner and outer surfaces, with a porous coating of metal beads affixed to substantially all of said outer surface to thereby provide a porous surface of interconnected three dimensional pores, said inner surface being substantially smooth; and
   an inert high density polymeric bearing having a substantially hemispherical shape and adapted to be attachably received within said cup and to receive the femoral head so as to permit said femoral head to articulate freely therein.

2. The hip joint prosthesis of claim 1 in which about 45% of the surface of the stem.

3. The hip joint prosthesis of claim 1 in which the collar extends beyond the stem on the medial side only.

4. The hip joint of claim 1 in which the porous coating on the stem has a pore size of at least 250 μm.

5. The hip joint of claim 1 in which the porous coating on the stem has a pore size of about 300 μm.

6. The hip joint of claim 1 in which the porous coating on the stem is at least 1 mm in thickness.

7. The hip joint of claim 1 in which the porous coating on the stem has a pore volume in excess of 40% but no more than 50%.

8. The hip joint of claim 1 in which the porous coating on the metal cup has a pore size of at least 250 μm.

9. The hip joint of claim 1 in which the porous coating on the metal cup has a pore size of about 300 μm.

10. The hip joint of claim 1 in which the porous coating on the metal cup is at least 1 mm in thickness.

11. The hip joint of claim 1 in which the porous coating on the metal cup has a pore volume in excess of 40% but no more than 50%.

12. The hip joint of claim 1 in which the femoral head has an opening therein tapered to correspond to the taper of the shaft portion of the stem, so that the femoral head may be used with stems of varying neck lengths.

13. The hip joint of claim 1 in which the acetabular cup has a plurality of radially positioned openings and one central sighting opening thereon to assure uniform intimacy with bone and for fastening means to attach the cup to the acetabulum.

14. The hip joint of claim 1 in which the acetabular means and the polymeric bearing means have groove and rim means, respectively thereon to snap fit and secure the acetabular cup means and polymeric bearing means together.

15. The hip joint of claim 1 in which the acetabular cup and the polymeric bearing means have cooperating locking means to secure the bearing means from rotating within the acetabular cup means.

16. The hip joint of claim 1 in which the intramedullary stem is made of a vacuum cast cobalt-chromium-molybdenum alloy and hot isostatically pressing both before and after the porous coating is applied, said alloy being inert to the surrounding body tissue and biological fluids.

17. The hip joint of claim 1 in which femoral head is made of a cobalt chromium molybdenum alloy that is inert to the surrounding body tissue and biological fluids.

18. The hip joint of claim 1 in which acetabular cup is made of a cobalt chromium molybdenum alloy that is inert to the surrounding body tissue and biological fluids.

19. The hip joint prosthesis of claim 1 wherein said neck angle is about 8°.

20. A hip joint prosthesis comprising, in combination:
an inert metal alloy intramedullary stem having posterior, proximal anterior and distal anterior surfaces defined by respective confluent arcs which enable said stem to anatomically conform to the femoral canal, said stem having a medial collar adjacent an upper end of a proximal portion of the stem, the collar extending medially outwardly from the stem for engagement with the calcar region of the femur, said upper end terminating in a shaft adapted to receive a femoral head component;
a porous metal coating extending over said proximal portion and an underside of said medial collar, such that said coating extends over about 45 percent of said stem, said coating adapted to mechanically interlock the proximal stem area with both soft cancellous and hard cortical bone tissue of the femur;
an inert metal alloy femoral head having a smooth substantially spherical outer bearing surface and adapted to be attached to the tapered shaft of the stem;
an inert metal alloy acetabular cup for attachment to the acetabulum, said cup having a substantially hemispherical shape and inner and outer surfaces, said outer surface having a porous metal coating affixed thereto; and
a substantially hemispherical shaped bearing adapted to fit within the cup and to receive the femoral head.

21. The hip joint of claim 20 in which the porous coating on the stem has a pore size of at least 250 μm.

22. The hip joint of claim 20 in which the porous coating on the stem has a pore volume in excess of 40% but no more than 50%.

23. The hip joint prosthesis according to claim 20 wherein the underside of said medial collar is surrounded by a lip which protects said porous metal coating.

24. The hip joint prosthesis of claim 20 wherein said cup is provided with a centrally located sighting aperture.

25. The hip joint prosthesis of claim 20 wherein said inner surface of said cup is provided with an annular ring groove and said bearing is provided on an exterior surface thereof with a complimentary snap ring groove adapted to matingly engage said annular ring groove to thereby secure said bearing within said cup.

* * * * *